United States Patent
Le Floch et al.

(10) Patent No.: US 10,631,382 B2
(45) Date of Patent: Apr. 21, 2020

(54) LIGHTING APPARATUS FACILITATING READING

(71) Applicants: Albert Le Floch, Rennes (FR); Université de Rennes 1, Rennes (FR)

(72) Inventors: Albert Le Floch, Rennes (FR); Guy Ropars, Rennes (FR)

(73) Assignee: UNIVERSITÉ DE RENNES 1, Rennes (FR)

( * ) Notice: Subject to any disclaimer, the term of this patent is extended or adjusted under 35 U.S.C. 154(b) by 0 days.

(21) Appl. No.: 15/883,233

(22) Filed: Jan. 30, 2018

(65) Prior Publication Data
US 2019/0159324 A1 May 23, 2019

(30) Foreign Application Priority Data

Nov. 20, 2017 (FR) ..................................... 17 01200

(51) Int. Cl.
| H05B 33/08 | (2020.01) |
| H05B 37/02 | (2006.01) |
| A61B 5/16 | (2006.01) |
| F21Y 115/10 | (2016.01) |

(52) U.S. Cl.
CPC .......... *H05B 37/0281* (2013.01); *A61B 5/165* (2013.01); *H05B 33/0815* (2013.01); *F21Y 2115/10* (2016.08)

(58) Field of Classification Search
CPC ............ H05B 33/0815; H05B 33/0845; H05B 37/0281; H05B 37/034
USPC .................................................. 315/307, 360
See application file for complete search history.

(56) References Cited

U.S. PATENT DOCUMENTS

| 3,842,822 A * | 10/1974 | Levinson | A61B 5/0496 600/558 |
| 8,076,858 B2 * | 12/2011 | Cheng | H05B 33/0818 315/153 |
| 2006/0279709 A1 * | 12/2006 | Yamamoto | G03B 21/2013 353/85 |
| 2011/0006707 A1 * | 1/2011 | Baaijens | H05B 33/0863 315/307 |
| 2014/0228914 A1 * | 8/2014 | van de Ven | A61N 5/0618 607/88 |
| 2015/0078743 A1 * | 3/2015 | Yang | H04B 10/116 398/38 |
| 2015/0163881 A1 * | 6/2015 | Pederson | H05B 33/0863 315/154 |
| 2015/0282277 A1 * | 10/2015 | Lewis | H05B 37/0218 340/815.45 |

(Continued)

OTHER PUBLICATIONS

Albert Le Floch, et al. Left-right Asymmetry of the Maxwell Spot Centroids in Adults Without and with Dyslexia, The Royal Society Publishing, Jun. 23, 2017, pp. 1-14.

*Primary Examiner* — Tung X Le
(74) *Attorney, Agent, or Firm* — Tutunjian & Bitetto, P.C.

(57) ABSTRACT

The invention relates to a lighting device (LIGHT) of a graphic and/or textual content represented on any support and in particular of the paper type, characterized in that a light beam generated in a visible light spectrum is activated and periodically deactivated from the lighting device (LIGHT) according to successive cycles operated at a predetermined frequency (Fd) and in that the successive illumination periods each have a duration (T1) within a range of values from 15 to 30% of the duration (T) of the operated cycles.

6 Claims, 1 Drawing Sheet

(56) References Cited

U.S. PATENT DOCUMENTS

2016/0302271 A1\* 10/2016 Fruitman ........... H05B 33/0815

\* cited by examiner

LIGHTING APPARATUS FACILITATING READING

1. FIELD OF THE INVENTION

The invention relates to a lighting device. The invention relates more particularly to a lighting device facilitating the reading of contents, especially textual, for persons prone to dyslexia.

2. BACKGROUND

Dyslexia is commonly defined as a set of reading disorders that appear in Childhood. These are specific learning disorders whose causes appear complex and have been and are still the subject of many studies in various fields.

It is generally excluded to consider that the causes of dyslexia are purely sensory, social or psychological.

Studies made in the field of neuroscience suggest that this may be a specific neurological disorder.

Advances made in the field of medical imaging have highlighted the role of certain areas of the brain in the process or reading and language proficiency.

The current solutions to treat disorders of dyslexia are based on work and play activities according to the difficulties that are specific to a given subject. The purpose of such accompaniment is to provide the troubled subjects with autonomy in reading. Known methods are developed around work in areas such as psychology, psychomotricity and orthoptics, for example.

Recently, studies have been conducted establishing a correlation between peculiarities of the mechanism of vision and the presence of dyslexia-specific disorders. The publication "Left-right asymmetry of the Maxwell spot centroids in adults without dyslexia" (Floch A, Ropars G. 2017, Proc. R. R. Soc. B 284: 20171380, http://dx.doi.org/10.1098/rspb.2017.1380) mentions the role of foveas, located in the human eye, in the construction of perceived images at the cerebral level, and the fact that identical or substantially identical characteristics for the two eyes of the same subject result in dysfunctions in the process of vision at the cerebral level. The transmission of a mirror image from one hemisphere to the other hemisphere of the brain significantly disturbs the process of reading graphic elements or textual contents in subjects with disorders characteristic of the dyslexia.

3. SUMMARY OF THE INVENTION

The invention improves at least some of the drawbacks of the prior art by proposing a lighting device adapted to facilitate the reading of contents, such as graphic contents, on any type of support, and in particular on a paper support. The proposed device operates successive periods of activation and deactivation or suppression of a light beam in the spectrum of visible light. The light beam is thus activated and deactivated (deleted) periodically from the lighting device in successive cycles operated at a predetermined frequency. The successive activation periods have each a duration in a range of values from 15 to 30% of the total duration of the operated cycles.

Advantageously, the predetermined frequency of the cycles thus operated is in a range of values from 60 to 90 Hz.

According to one embodiment of the invention, the beam produced in a visible light spectrum is generated from one or more LED-type elements.

Advantageously, the use of a frequency range beginning from 60 Hz overcomes the effects of blinking perceptible by the eye of the human being, the limit of perception of blinking by the eye being around 60 Hz, for humans (excluding animals and insects).

Advantageously, the alternation of periods of activation and suppression of the light beam, established in the spectrum of visible light and applied to (oriented towards) a support, allows a "focusing" of the brain of a subject looking at this illuminated support, on an image representative of the content represented on the observed support, and then, a disappearance of this same image from the view of the subject before it is transmitted as a mirror image between one cerebral hemisphere and the other cerebral hemisphere, for this subject looking at this illuminated support. The time required for the brain to transmit an image, perceived by the eye, between one hemisphere and the other hemisphere of the brain, in the form of a mirror image for the latter, is of the order of 10 ms.

Thus, the brain privileges the transmitted image with respect to its mirror image, and the confusion existing in the subject which has a strong similarity of the characteristics of its two foveas, is less or substantially diminished for the reading of the content (graphic and/or textual) represented on the support, especially when this content is representative of one or more textual contents.

4. LIST OF FIGURES

The invention will be better understood, and other features and advantages will appear on reading the description which follows, the description referring to the appended drawings among which:

5. DETAILED DESCRIPTION OF AN EMBODIMENT OF THE INVENTION

Figure 2:
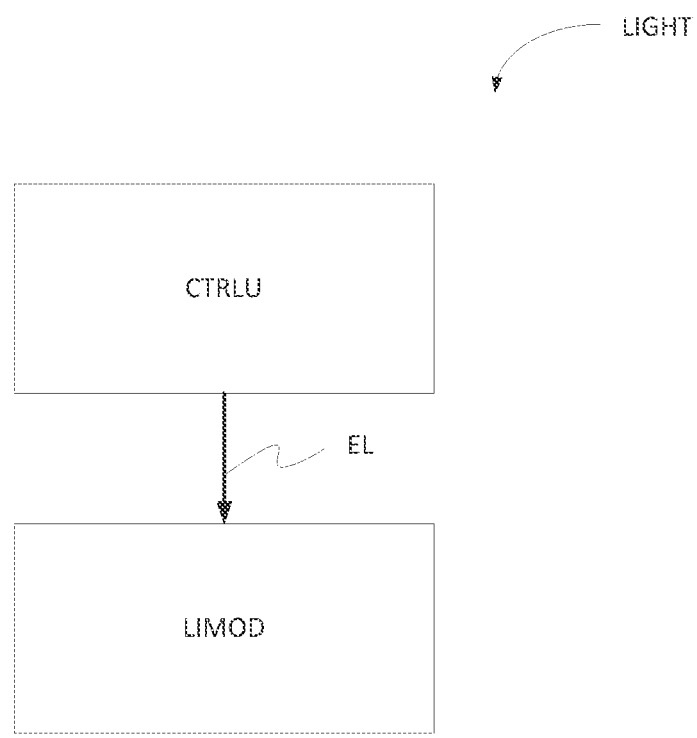
FIG. 2 is a structural representation of the architecture of a LIGHT lighting device according to a particular and non-limiting embodiment of the invention.

In FIG. 2, the modules shown are functional units, which may or may not correspond to physically distinguishable units. For example, these modules or some of them are grouped into a single component. In an opposite way, according to other embodiments, some modules are composed of separate physical entities.

Figure 1:
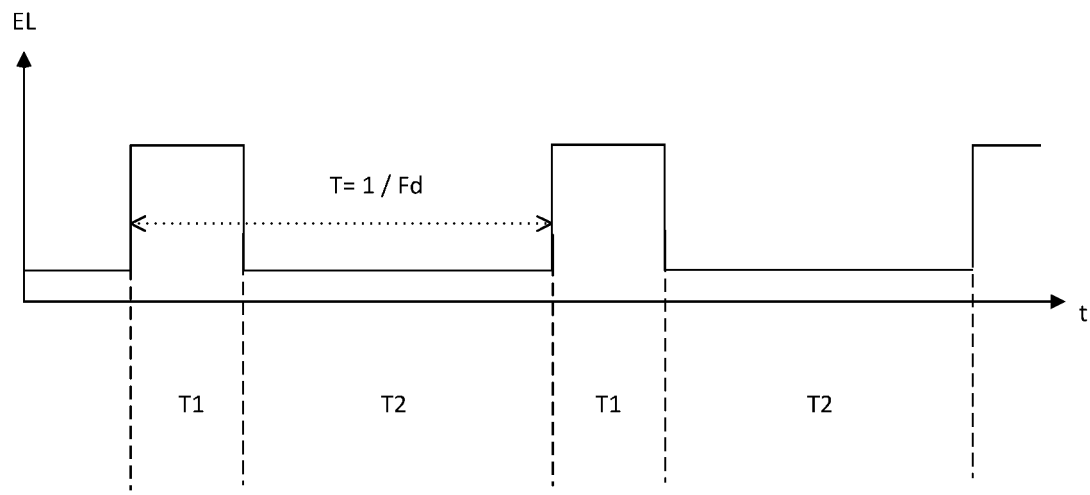
FIG. 1 is a representation diagram of an EL control signal of a lighting module according to a particular and non-limiting embodiment of the invention.

FIG. 1 is a temporal representation of an EL control signal for activating and deactivating (deleting) a light beam in the visible light spectrum, in a LIGHT lighting device, according to a mode of particular and non-limiting embodiment of the invention. The signal EL varies according to the time t and periodically takes two successive states. According to the preferred embodiment, an assertion of the signal EL in the high state controls an activation of the lighting beam of the lighting device LIGHT, which can thus illuminate, in a discontinuous manner, a graphic and/or textual content on a support whatever, such as a book, for example. The EL signal deactivates (removes or inhibits) the light beam of the lighting module when it is set low. The signal EL is a periodic signal of predetermined frequency Fd such that $Fd=1/(T1+T2)$. $T1$ is the period of activation of the light beam in the visible light spectrum, ie the illumination period of a support bearing a pattern representing a graphic and/or textual content towards which the beam is oriented. $T2$ is the period during which the beam is deleted or rendered inactive, or in other words the period during which the graphic and/or textual content on a support towards which the beam is oriented is no longer illuminated by the beam. The terms "graphic content" are to be interpreted here as any content represented on any medium, in particular in paper format but not only, and constituted by elementary elements such as, for example, points or pixels juxtaposed, so that the content represents elements of various forms including one or more textual contents constructed from signs or symbols of one or more alphabets.

Thus, a textual content affixed to a medium corresponds here to an interpretable content in one or more languages, which can be read and interpreted by a subject, a user of the lighting device, positioned so as to look at the support thus illuminated for an operation as reading or viewing. Such a device is, for example, a desk lamp, a flashlight, a headlamp, a pen-lamp, a flashlight, a telephone lamp, a smartphone lamp, a lamp-watch, a key lamp, ceiling lamp, floor lamp, bulb, light tube, projector, car headlamp, overhead projector, bright wall cladding, light carpet, light bracelet, light frame, mini-lamp to be positioned on a book by means of a fastening system, a device configured for interior lighting (of a room) or a device configured for outdoor lighting, urban or otherwise. This list of examples is not exhaustive. According to the preferred embodiment of the invention, the duty cycle $T1/(T1+T2)$ between the periods of activation and deactivation (or inhibition) of the light beam, respectively of durations $T1$ and $T2$, has a value between 15% and 30% of the whole cycle, and the frequency Fd of variation of the EL signal is between 60 Hz and 90 Hz.

Preferably, the frequency of the signal is equal to 70 Hz or 84 Hz and the duty cycle $T1/(T1+T2)$ is equal to 20%.

Advantageously, the control signal EL can be easily forced to prolong its state associated with an activation of the light beam, which corresponds to a disengagement of the lighting method implemented in the LIGHT device according to the invention. It would thus be possible not to implement the method of controlling a light beam, in a lighting device according to the invention, in the case where, for a non-dyslexic subject, a visual discomfort would appear because of the discontinuity of activation of the illumination beam.

Advantageously, it is possible to refine the adjustment of the frequency Fd in the range of values described in order to adapt the period T to the sensitivity of a user of the lighting device LIGHT, within the indicated frequency range. Indeed, each individual has is own sensitivity in terms of vision and perceives more or less frequency variations of a light beam. Thus, a fine-tuning can be made accessible to the user by means of an adjustment button, a cursor, implemented in hardware or via any user interface (graphic elements of a menu on a control screen, for example).

FIG. 2 is a structural representation of a lighting device LIGHT according to a particular and non-limiting embodiment of the invention. This figure represents the overall architecture of the LIGHT lighting device, still commonly called "lamp". The LIGHT device comprises two main modules which are a CTRLU control unit and a LIMOD lighting module. The control unit CTRLU is the heart of the system in terms of control and comprises a conventional bistable circuit (or chopper), adapted to the generation of the EL signal. The bistable chopping circuit of the control unit CTRLU delivers the signal EL characterized by the frequency Fd and by its duty cycle $T1/(T1+T2)$. Of course, the control unit CTRLU comprises all the usual elements implemented in such an architecture, such as, for example, one or more operational amplifiers, resistors and capacitors, one or more diodes, a power supply, a resetting circuit, a power supervision circuit, a power interface, a current amplifier, the list of these elements is not exhaustive. The architectural details of the control unit CTRLU are not described further to the extent that they are not useful for understanding the invention. According to one embodiment of the invention, the CTRLU module comprises a bistable circuit built around an operational amplifier, coupled to a current amplification circuit. Advantageously, the use of a current amplifier makes it possible to obtain sufficient average energy at a correct illumination even though the light beam thus generated is discontinuous. The LIMOD lighting module is a lighting module suitable for generating a light beam in the spectrum of visible light, or substantially wider. Advantageously, the beam may be more or less focused to be configured for lighting a larger or smaller surface. Such a focus can be achieved by the use of optical elements (lenses) or mechanical elements (diaphragms), or both.

Advantageously, the light beam is made from one or more LED type electroluminescent objects, from the acronym "Light-Emitting Diode". Of course, the light beam can be made from other light elements, considering the deactivation of the beam can be fast enough to respect the cycles comprising lighting periods and beam inhibition (periods of non-light).

The term "beam inhibition" should be interpreted here as a total disappearance of the beam or a consequent decrease in the level of illumination produced by the beam.

it is the ability to activate and successively inhibit the illumination of a medium that has one or more graphic and/or textual contents, under the control of the bistable module of the CTRLU unit, which advantageously allows the brain of a subject to prefer (focus on) an image rather than its mirror image, perceived from the support when the latter is illuminated by the LIGHT lighting device according to the invention. Advantageously, this makes it possible to help consequently the reading and the deciphering of textual contents, in a subject having dyslexic disorders.

Advantageously, the control unit CTRLU comprises (controls) an output signal EL activation (or extinction/inhibition) of the lighting beam, connected to the input of the lighting module LIMOD.

In other words, the variations of the illumination beam control signal EL, made by the control unit CTRLU comprising a bistable circuit at a frequency Fd, act on the lighting of a graphic content, represented on any support, so that this graphic content is successively lit then less (or more at all) illuminated, periodically, on the support, in successive cycles of total length T operated at a predetermined frequency Fd. According to the invention, the successive illumination periods $T1$ each have a duration in a range of values ranging from 15 to 30% of the duration T of said operated cycles.

The invention is not limited to the embodiments described above, but applies to any lighting device of a graphic and/or textual content on any medium, implementing successive activation operations, a beam of illumination and inhibition of this same beam, periodically, according to successive cycles operated at a predetermined frequency Fd between 60 Hz and 90 Hz such that successive lighting periods $T1$ each have a duration included in a range of values ranging from 15 to 30% of the duration T cycles operated.

The invention claimed is:

1. A lighting device for facilitating the reading of graphical and/or textual content printed on a medium for persons prone to dyslexia, the lighting device comprising:

a control unit; and
a lighting module configured to provide illumination in a visible light spectrum, of the graphical and/or textual content printed on the medium, said control unit and said lighting module being configured to:
periodically activate and deactivate said illumination in successive cycles operated at a predetermined frequency between 60 Hz and 90 Hz, said predetermined frequency being a reciprocal of a sum of a period of activation of said illumination and a period of non-activation of said illumination; and
operate successive illumination periods each having a duration in a range of 15 to 30% of said successive cycles.

2. The lighting device according to claim 1, wherein said illumination is generated from one or more LED-type elements.

3. The lighting device according to claim 1, wherein said device is one selected from a group consisting of: a desk lamp, a flashlight, a headlamp, a pen-lamp, a flashlight, a telephone lamp, a smartphone lamp, a lamp-watch, a key-door lamp, a ceiling lamp, a lamp-post, a bulb, a lighting tube, a projector, an automobile projector, an overhead projector, a luminous wall covering, a light carpet, a luminous bracelet, a light frame, a mini-lamp to be positioned on a book, a device configured for interior lighting and a device configured for outdoor lighting, urban or otherwise.

4. A lighting device for facilitating the reading of graphical and/or textual content printed on paper for persons prone to dyslexia, the lighting device comprising:
a control unit; and
a lighting module configured to provide illumination in a visible light spectrum, of the paper and graphical and/or textual content printed thereon, said control unit and said lighting module being configured to:
periodically activate and deactivate said illumination in successive cycles operated at a predetermined frequency between 60 Hz and 90 Hz, said predetermined frequency being a reciprocal of a sum of a period of activation of said illumination and a period of non-activation of said illumination; and
operate successive illumination periods each having a duration in a range of 15 to 30% of said successive cycles.

5. The lighting device according to claim 4, wherein said illumination is generated from one or more LED-type elements.

6. The lighting device according to claim 4, wherein said device is one selected from a group consisting of: a desk lamp, a flashlight, a headlamp, a pen-lamp, a flashlight, a telephone lamp, a smartphone lamp, a lamp-watch, a key-door lamp, a ceiling lamp, a lamp-post, a bulb, a lighting tube, a projector, an automobile projector, an overhead projector, a luminous wall covering, a light carpet, a luminous bracelet, a light frame, a mini-lamp to be positioned on a book, a device configured for interior lighting and a device configured for outdoor lighting, urban or otherwise.

\* \* \* \* \*